United States Patent [19]

Bhatia et al.

[11] Patent Number: 4,758,371
[45] Date of Patent: Jul. 19, 1988

[54] PROCESS AND COMPOSITION FOR REMOVAL OF MERCAPTANS FROM GAS STREAMS

[75] Inventors: Kishan Bhatia, Katy; John G. Garcia, Jr., Houston, both of Tex.

[73] Assignee: NL Industries, Inc., New York, N.Y.

[21] Appl. No.: 62,207

[22] Filed: Jun. 15, 1987

Related U.S. Application Data

[62] Division of Ser. No. 838,379, Mar. 11, 1986.

[51] Int. Cl.⁴ .............................................. C09K 3/00
[52] U.S. Cl. .................................... 252/192; 252/189
[58] Field of Search ................................ 252/192, 189

[56] References Cited

U.S. PATENT DOCUMENTS

| | | |
|---|---|---|
| 2,164,851 | 7/1939 | Yabroff et al. . |
| 2,369,771 | 2/1945 | Bond . |
| 2,413,945 | 1/1947 | Bolt . |
| 2,446,507 | 8/1948 | Cauley . |
| 3,391,988 | 7/1968 | Friess . |
| 3,644,087 | 2/1972 | Urban . |
| 3,843,771 | 10/1974 | Urban .............................. 423/242 X |
| 4,141,961 | 2/1979 | Miller .......................... 423/242 A X |
| 4,210,526 | 7/1980 | Swanson . |
| 4,412,913 | 11/1983 | Moote et al. . |
| 4,460,395 | 7/1984 | Nobles et al. . |
| 4,462,968 | 7/1984 | Tazuma et al. . |
| 4,515,759 | 5/1985 | Burnes et al. . |
| 4,540,552 | 9/1985 | Ream et al. . |

FOREIGN PATENT DOCUMENTS 10931 3/1896 United Kingdom ................ 252/192

*Primary Examiner*—Matthew A. Thexton
*Attorney, Agent, or Firm*—Browning, Bushman, Zamecki & Anderson

[57] ABSTRACT

A composition and process for the removal of mercaptans from gaseous mixtures, particularly gaseous mixtures containing hydrocarbons, wherein the gaseous mixture is treated with an aqueous solution of a water soluble nitrite, such as sodium nitrite, and a water soluble polysulfide, such as sodium tetrasulfide, the pH of the aqueous solution preferably being about 10 or greater initially.

8 Claims, No Drawings

PROCESS AND COMPOSITION FOR REMOVAL OF MERCAPTANS FROM GAS STREAMS

This is a division of application Ser. No. 838,379, filed Mar. 11, 1986.

BACKGROUND OF THE INVENTION

The present invention relates to the removal of mercaptans or thioalcohols, from gas mixtures, particularly gas mixtures containing hydrocarbons such as, for example, natural gas.

The removal of sulphur compounds from gas streams has been of considerable importance in the past and is of greater importance today due to environmental concerns. Gas effluent from the combustion of organic materials, such as coal, almost always contains sulfur compounds and sulfur removal processes have concentrated on removing these sulfur compounds since it has been determined that some of them pose significant health hazards. With increasing emphasis on the elimination of sulfur discharge to the atmosphere and utilization of natural gas streams that were heretofore unusable due to their sulfur content, attention is turning to the removal of sulfur compounds from gas streams.

Numerous natural gas wells produce what is called in the industry "sour gas". Sour gas is natural gas that contains sulfur compounds, especially hydrogen sulfide, in concentrations that make its use unacceptable as for example in home heating uses, refinery feed gases, etc. Considerable effort has been expended in finding effective and cost efficient processes to remove these objectionable sulfur compounds from natural gas. There has been extensive work done in developing process for the removal of hydrogen sulfide from gas treatments such as natural gas streams. Indeed, the patent literature is replete with processes for the removal of $H_2S$ from natural gas streams as well as other gas streams containing $H_2S$.

There are some natural gas streams which are "sour", not because they contain hydrogen sulfide but because they contain objectionable levels of mercaptans. Insofar as the end use of these natural gas streams are concerned, the mercaptans are virtually as objectionable as hydrogen sulfide, mainly because of odor, albeit that for the most part they are not as toxic as hydrogen sulfide.

Examples of patented processes for the removal of mercaptans from gas streams include U.S. Pat. Nos. 4,412,913; 4,462,968; 4,540,552; 4,460,395. U.S. Pat. No. 4,515,759 discloses a process for removing hydrogen sulfide from gas mixtures by treating the gas mixture with an aqueous medium containing a water soluble nitrite such as sodium nitrite. However, the patent does not disclose the removal of mercaptans or other similar organic sulfide compounds from gas streams.

SUMMARY OF THE INVENTION

It is therefore an object of the present invention to provide a novel process for the removal of mercaptans from gas mixtures.

Another object of the present invention is to provide a composition useful in a process for removing mercaptans from gas mixtures.

The above and other objects of the present invention will become apparent from the description given herein and the claims.

The process of the present invention comprises treating, e.g. scrubbing, a gas mixture containing at least one mercaptan with an aqueous medium containing an effective amount of an inorganic, water soluble nitrite and an effective amount of a water soluble polysulfide.

The composition of the present invention comprises an aqueous medium containing an effective amount of an inorganic, water soluble nitrite and an effective amount of a water soluble polysulfide, the initial pH of the aqueous medium being about about 10 or above.

DESCRIPTION OF THE PREFERRED EMBODIMENT

Gas mixtures particularly suited to removal of mercaptans according to the process of the present invention are naturally occurring gases, synthesis gases, process gases, fuel gases produced by gasification procedures, e.g. gases produced by the gasification of coal, petroleum, shale, tar, sands, etc. Particularly preferred are natural gas streams, coal gasifications streams and refinery feed stocks composed of gaseous hydrocarbon streams and other gaseous hydrocarbon streams. The term "natural gas" or "natural gas stream", as used herein, refers to a mixture of gases comprising primarily methane with smaller amounts of at least one of the following components: nitrogen, carbon monoxide, carbon dioxide, or ethane. The term "hydrocarbon stream(s)", as employed herein, is intended to include streams containing significant quantities of hydrocarbons (parafins, olefins, and aromatics), it being recognized that such streams contain significant "impurities" not technically defined as a hydrocarbon. Again, streams containing principally a single hydrocarbon, e.g. methane, are eminently suited to the practice of the present invention. Streams derived from the gasification and/or partial oxidation of gases or liquid hydrocarbons may be treated by the invention. Indeed, the process can be used with any gas stream containing mercaptans that does not contain components other than $H_2S$ or mercaptans which will selectively react, to any appreciable degree, with the active components of the scrubbing medium, i.e. the soluble nitrite and the soluble polysulfide. The mercaptan content of the type of gas stream contemplated with vary extensively, but, in general, will range from about 0.001% to about 15% by volume. Obviously, the content of mercaptans and the composition of the gaseous mixture is not a limiting factor in the practice of the process of the present invention.

The mercaptans which can be removed according to the process of the present invention include any mercaptan or thioalcohol that is present in a gaseous mixture, either as a vapor or as an entrained liquid and which is soluble in water, or can be solubilized in an aqueous medium containing a water miscible co-solvent. Generally speaking, the present invention is best suited to the removal of mercaptans which have some appreciable vapor pressure so as to be present in gaseous form in a gas mixture at 100° F. Non-limiting examples of such mercaptans include methyl mercaptan, ethyl mercaptan, n-propyl mercaptan, isopropyl mercaptan, n-butyl mercaptan, sec-butyl mercaptan, isobutyl mercaptan, tert-butyl mercaptan, amyl mercaptan, etc. The present invention is especially suited to the removal of mercaptans containing from 1 to 4 carbon atoms since such mercaptans exhibit apprecicate vapor pressures at 100° F., have appreciable solubility in water and are found in many gaseous streams.

The present invention utilizes an aqueous medium, which may be considered a scrubbing or contacting medium, containing a water soluble nitrite and a water soluble polysulfide. The term "aqueous medium" is intended to include solutions as well as slurries or other aqueous mixtures. Indeed, as the treatment of the gas mixture containing the mercaptans proceeds according to the process of the present invention, elemental sulfur may be formed so that the aqueous medium, while it may initially be a true solution, becomes a slurry containing the soluble unreacted nitrite, polysulfides, various oxidation product of the mercaptans and particulate, elemental sulfur. The aqueous medium can comprise water alone as the liquid component or can include a solution of water and a water miscible organic liquid which is a solvent for the mercaptans and which will aid in solubilization of the mercaptan in the aqueous medium. Non-limiting examples of such organic liquids include lower alcohols which are water soluble, waters miscible ketones, etc. The water miscible liquid should be one which does not react in the aqueous medium under the treatment conditions. When used the water miscible liquid will be present in an amount of from about 1 to about 10% by volume of the aqueous medium.

The water soluble nitrites useful in the process of the present invention, generally speaking, are inorganic nitrites, particularly the alkali and alkaline earth metal nitrites such as, for example, sodium nitrite, potassium nitrite, lithium nitrite, calcium nitrite, magnesium nitrite, etc. Such metal nitrites are characterized by high solubility in water and, in the case of sodium nitrite, are relatively inexpensive. In addition, ammonium nitrite may be employed although it will be recognized that ammonium nitrite is extremely dangerous to use because of its explosive characteristics. Heavy metal nitrites, while they will function, are less desirable because of their greatly reduced solubility in water. Moreover, heavy metal nitrites are somewhat more hazardous to handle since thermally, they are much less stable than the alkali or alkaline earth metal nitrites. In general, any water soluble metal nitrite or ammonium nitrite can be employed. Particularly preferred because of their ready availability and high solubility are the alkali metal nitrites, particularly sodium nitrite.

The concentration of the water soluble nitrite in the aqueous medium can vary widely depending upon the mercaptan concentration of the gaseous mixture, the desired degree of mercaptan removal, the volume of gaseous mixture being treated, the type of treatment apparatus employed, the composition of the gas mixture and other such parameters. In general, only an effective amount need be present, such an amount being readily determinable by knowing the concentration of mercaptans initially in the gas stream. However, and generally speaking, in the preferred case, the water soluble nitrite will be present in an amount of from about 0.1% to about saturation, more particularly from about 5% to about 40% by weight, calculated as nitrite.

The polysulfide used in the process of the present invention can be generally described as a water soluble organic or inorganic polysulfide compound comprising unbranched chains of sulfur atoms of the form $S_n^{--}$ where n is 2, 3, 4, 5 or 6. Thus, the ions of polysulfide chains may be depicted structurally as follows:

$(S-S-S-S)^{--}$ in the case of a tetrasulfide. Although it has been observed that $S_4^{--}$ and $S_5^{--}$ are the dominant species of polysulfides, it is believed that the species $S_2^{--}$ and $S_3^{--}$ also exist although they are believed to be unstable and quickly reacted. In any event, insofar as known to the inventors, the polysulfide species wheren n is 4 and 5 are generally the predominantly occurring species, it being understood that generally a mixture of the various species may be present. Polysulfides such as, for example, sodium polysulfide, may be synthesized by reacting sodium chloride with potassium polysulfide ($K_2S_n$) yielding $Na_2S_n$. Alternatively, sodium and solid sulfur can be reacted to form sodium polysulfides in high yields and purity.

The polysulfide has an apparent catalytic effect on the ability of the nitrite solution to oxidize the mercaptan and remove it from the gas stream. This mechanism is not fully understood by the inventors. While it may be that one of the polysulfide species, as described above, is responsible for the catalytic effect observed, it is also possible that the polysulfides which are generally thermodynamically unstable in an oxidizing environment such as that provided by a nitrite solution are converted or "oxidized" to unidentified intermediates which form the catalytic species to promote the oxidation of the mercaptan. Accordingly, it is to be understood that the term "polysulfide" includes any unidentified species thereof formed from such polysulfide in the oxidizing medium and which is ultimately responsible for the catalysis of the reaction between the nitrite oxidant and the mercaptan. Although any water soluble polysulfide will function in the process of the present invention, particularly preferred, because of high water solubility and ready availability, are inorganic polysulfides, especially the alkali metal polysulfides, e.g. sodium polysulfide, potassium polysulfide, etc. Sodium tetrasulfide is especially preferred. However, other inorganic polysulfides such as alkaline earth metal polysulfide, e.g. calcium polysulfide, or other, heavy metal polysulfide, as well as organic polysulfides will function provided they have sufficient water solubility and stability in the aqueous scrubbing medium to effect the desired catalytic effect in the reaction between the nitrite and the mercaptan in the gas being scrubbed.

The concentration of the polysulfide in the aqueous medium can vary widely depending generally upon the same variables used to determine the concentration of the water soluble nitrite. In general, only an effective amount need be present, where an effective amount is defined as that amount which enhances reaction between the nitrite and the mercaptans to effect oxidation of the latter. Thus, the polysulfide can be present from a minute amount up to saturation. Generally speaking, however, the polysulfide will be present in an amount of from about 0.1 to about 10% by weight of the scrubbing medium calculated as tetrasulfide, more preferably from about 1 to about 10% by weight, it being understood that the polysulfide may be present in other forms such as $S_3^{--}$ or $S_5^{--}$, as noted above. When employing sodium tetrasulfide solution containing about 34% by weight sodium tetrasulfide, amounts of the tetrasulfide solution ranging from about 3 to about 20% by volume of the aqueous medium can be conveniently used.

Although the polysulfide used in the process of the present invention can be manufactured, in situ, in the scrubbing medium, it is preferred that it be added in the form of an aqueous solution. A convenient method to add the polysulfide is to use a commercially available sodium tetrasulfide solution containing approximately 34% by weight sodium tetrasulfide.

In initially forming the composition of the present invention, the pH of the aqueous medium should be at about 10 or greater. It has been observed that if the pH of the initial aqueous medium containing the nitrite and polysulfide is lower than 10, there is an initial evolution of $H_2S$ from the scrubbing medium formed by the polysulfide. It is hypothesised that it is necessary to form the proper catalytic species of the polysulfide before the reaction between the nitrite and the mercaptan can occur. Apparently, this catalytic species will not initially form at low pH values, i.e. lower than 10. Accordingly, a convenient method of forming the composition of the present invention is to first prepare the aqueous medium containing the nitrite and suitable base or buffering agents to raise the pH to above about 10 and then add the sodium tetrasulfide or other polysulfide. The aqueous medium, thus prepared, can then be used to immediately commence scrubbing the gas containing the mercaptan without any evolution of $H_2S$ from the scrubbing medium.

In conducting the process of the present invention, and after the polysulfide has been added and scrubbing commenced until the catalytic species of the polysulfide has formed, it is necessary that the pH be maintained, above about 5.5, preferably above 7. At lower pH values, the nitrite decomposes leading to consumption of the active nitrite and the formation of excessive amounts of nitrogen oxides ($NO_x$). Additionally, $SO_2$ is formed at lower pH values and is vented in the off gas. Additionally, the polysulfide shows limited solubility at pH values lower than 7. Generally speaking, it is preferred that the pH of the aqueous medium be maintained in a range of from about 7 to about 12, and more preferably from about 8 to about 12.

The aqueous medium can contain a suitable buffering agent to achieve proper pH control. Many gas streams containing mercaptans also contain $CO_2$ and other acid gases which are readily absorbed and which can cause swings in the pH values. On the other hand, the presence of a buffering agent which maintains the aqueous medium in a pH of from about 7 to about 12 will help to prevent any rapid lowering of pH should an acid contaminant unexpectedly be introduced into the system and which, in the absence of the buffer, would lower the pH to below 7. Non-limiting examples of suitable buffering agents include borates such as sodium borate; phosphates such as potassium dihydrogen phosphate; bicarbonates, such as sodium bicarbonate; carbonates such as sodium carbonate in admixture with caustic; phthalates, such as potassium hydrogen phthalate; ammonium chloride buffers and mixtures thereof. It will be understood that such buffering agents will be admixed with the requisite amounts of various acids and bases to obtain the desired pH. Non-limiting examples of suitable buffering agents and methods in preparation therefore set forth in "Buffer Solutions Operational Definitions of pH," R. A. Robinson, *Handbook of Physics and Chemistry*, 61st Edition, incorporated herein by reference.

The "treatment" of gaseous mixtures containing mercaptans contemplates any method by which the gaseous mixture is brought into intimate contact with the aqueous scrubbing medium containing the water soluble nitrite and the polysulfide. Thus, the gaseous mixture may be contacted with the aqueous medium in any conventional gas liquid contactor. For example, the aqueous medium may be sprayed over the gas mixture or a packed tower may be used. The gas may be bubbled through a vessel, e.g. in a bubble tower, containing the aqueous medium or the gas mixture and aqueous medium may be contacted in a counter current gas liquid extractor. It will be readily apparent to those skilled in the art that many other methods of effecting treatment or scrubbing of the gas mixture with the aqueous medium can be employed. Therefore, it is contemplated that any manner of contacting of the gas mixture with the aqueous scrubbing medium sufficient to effect reaction between the mercaptans and the active ingredients of the scrubbing medium can be employed and are suitable in the process of the present invention.

The particular method of treatment of the gaseous mixture, whether it be referred to as contacting, scrubbing or the like, should be such as to permit a contact time between the gaseous mixture and the aqueous medium sufficiently long to ensure reaction of the mercaptans with the active ingredients of the scrubbing medium. It will be appreciated that the contact time can vary considerably depending on the mercaptan content of the gas, gas flow rates, volume of aqueous scrubbing medium, temperatures, types of scrubbing vessels or equipment employed, etc. In general, however, contact times ranging from about 0.01 second to 360 seconds or longer can be employed.

Temperatures employed in the process of the present invention are generally not critical, although higher temperatures generally promote speed of reaction. While the process can be conducted at ambient temperatures, temperatures of from about 10° C. to about 80° C. are suitable, temperatures from about 20° C. to about 60° C. being preferred.

Pressure conditions in the process may also vary widely. For example, pressures in the process may vary from one atmosphere up to several hundred atmospheres, pressures of from about one atmosphere to about 50 atmospheres being preferred, particularly in the case of natural gas streams. The pressure-temperature relationships involved in gas contacting and scrubbing processes are well understood by those skilled in the art, and need not be detailed herein.

In order to more fully illustrate the present invention, the following non-limiting examples are presented. In the examples which follow, the scrubbing apparatus employed consisted of a specially designed glass bubble tower having a height of 105 cm and a diameter of 8 cm. In all cases, 4000 ml of aqueous medium was employed. The tower was operated at atmospheric pressure and a temperature of from about 68°-70° F. Unless otherwise indicated, the gaseous mixture utilized consisted of methane, 3% carbon dioxide and 1,000 ppm of the mercaptan. The mercaptan content of the outlet gas stream was determined by Drager tubes or Sensidyne tubes. A typical run consisted of maintaining gas flow (2200 ml/min) through the bubble tower for a desired period of time, the effluent gas being monitored at various intervals to determine the mercaptan content.

EXAMPLE 1

The bubble tower was charged with 4000 ml of an aqueous scrubbing medium having the following composition:
40% by weight $Na_2NO_2$;
1% by weight NaOH solution (50% by weight NaOH);
1% by weight $Na_2CO_3$.
$H_2O$ (balance).
The solution had an initial pH of 12 which reached an equilibrium pH of about 8.0 after about 100 minutes of gas flow through the bubble tower. In this example the mercaptan used was methyl mercaptan. The results are given in Table 1 below.

TABLE 1

| Minutes | ppm CH$_3$SH (outlet gas) |
|---|---|
| 0 | — |
| 15 | 0 |
| 50 | 0 |
| 90 | 0 |
| 105 | 20 |
| 120 | 30 |
| 150 | 60 |
| 180 | 160 |
| 210 | 1,000 |
| 270 | 1,000 |
| 300 | 1,000 |
| 330 | 1,000 |
| 360 | 1,000 |
| 390 | 1,000 |
| 410 | 1,000 |

It can be seen from the data in Table 1 that after approximately 100 minutes, the methyl mercaptan in the outlet gas began to rise very rapidly reaching a level of approximately 1000 parts per million after 210 minutes. This shows that the nitrite solution disclosed in U.S. Pat. No. 4,515,759 has no effect on removal of the methyl mercaptan from the gas stream. The initial, low level of methyl mercaptan in the outlet gas observed can be attributed to the water solubility of the methyl mercaptan in the aqueous scrubbing medium and not to any removal of the mercaptan due to oxidation or other reaction.

EXAMPLE 2

The procedure of Example 1 was followed with the exception that the aqueous scrubbing medium contained, in addition, 3% by volume of a sodium tetrasulfide solution (34% by weight sodium tetrasulfide). The initial pH of the aqueous medium was about 12. The data is shown in Table 2 below.

TABLE 2

| Minutes | ppm CH$_3$SH (outlet gas) |
|---|---|
| 0 | — |
| 15 | 0 |
| 50 | 0 |
| 90 | 0 |
| 105 | 0 |
| 120 | trace |
| 150 | 0 |
| 180 | 10 |
| 210 | 40 |
| 270 | 200 |
| 300 | 300 |
| 330 | 300 |
| 360 | 400 |
| 390 | 400 |
| 410 | 400 |

The data in Table 2 demonstrate that by using an aqueous scrubbing medium containing 3% by volume sodium tetrasulfide solution (34% by weight sodium tetrasulfide solution), there is some reduction in the methyl mercaptan outlet gas, i.e. some of the methyl mercaptan is being oxidized. However, it is to be observed that the scrubbing medium containing only 3 percent by volume of the sodium tetrasulfide solution has limited effectiveness since the outlet gas, after the initial period in which the methyl mercaptan solubilizes in water, contains approximately 400 parts per million indicating that the scrubbing medium has removed approximately 600 parts per million of the methyl mercaptan.

EXAMPLE 3

The procedure of Example 2 was followed with the exception that the gas being scrubbed contained 3000 ppm H$_2$S, 100 ppm CH$_3$SH, 3% CO$_2$ and the balance methane. The data are shown in Table 3 below:

TABLE 3

| Minutes | ppm CH$_3$SH (outlet gas) |
|---|---|
| 0 | — |
| 45 | 0 |
| 105 | 10 |
| 165 | 20 |
| 195 | 40 |
| 255 | 30 |
| 300 | 30 |
| 345 | 40 |
| 375 | 40 |
| 435 | 40 |
| 465 | 40 |

As can be seen from the data in Example 3, even in the presence of significant amounts of H$_2$S, the scrubbing solution containing the sodium tetrasulfide still effects approximately 60% removal of the methyl mercaptan from the gas.

EXAMPLE 4

The procedure of Example 3 was followed with the exception that the scrubbing medium contained 6 volume percent of sodium tetrasulfide solution (34% by weight sodium tetrasulfide). The data are shown in Table 4 below:

TABLE 4

| Minutes | ppm CH$_3$SH (outlet gas) |
|---|---|
| 0 | — |
| 40 | 0 |
| 90 | 2 |
| 150 | 5 |
| 210 | 10 |
| 240 | 10 |
| 270 | 10 |
| 300 | 10 |

It can be seen from the data in Table 4 that when the scrubbing medium contains 6 volume percent of the sodium tetrasulfide solution approximately 90% of the removal of the methyl mercaptan from the gas stream is accomplished even in the presence of 3000 ppm H$_2$S.

EXAMPLE 5

The procedure of Example 3 was followed with the exception that the scrubbing medium contained 12 volume percent of sodium tetrasulfide solution (34% by weight sodium tetrasulfide.) The data are given in Table 5 below.

TABLE 5

| Minutes | ppm CH$_3$SH (outlet gas) |
|---|---|
| 0 | — |
| 40 | 0 |
| 90 | 0 |
| 150 | 5 |
| 210 | 5 |
| 240 | 5 |

TABLE 5-continued

| Minutes | ppm CH₃SH (outlet gas) |
|---|---|
| 270 | 5 |
| 300 | 5 |

It can be seen from the data in Table 5 that where the concentration of sodium tetrasulfide is 12% by volume, there is approximately 95% removal of the methyl mercaptan even in the presence of 3000 parts per million $H_2S$.

The data in Tables 2–5 demonstrate that to remove 90% or greater of the methyl mercaptan from the gas stream, the aqueous scrubbing medium should contain at least 6% by volume of a sodium tetrasulfide solution containing 34% by weight sodium tetrasulfide.

EXAMPLE 6

The procedure of Example 2 was followed with the exception that the gas being scrubbed contained 1000 ppm $CH_3SH$ and the scrubbing medium contained 6 volume percent of a sodium tetrasulfide solution containing 34% by weight sodium tetrasulfide. The data are given in Table 6 below.

TABLE 6

| Minutes | ppm CH₃SH (outlet gas) |
|---|---|
| 0 | — |
| 25 | 10 |
| 55 | 40 |
| 85 | 60 |
| 115 | 60 |
| 145 | 60 |
| 205 | 70 |

EXAMPLE 7

The procedure of Example 2 was followed with the exception that the scrubbing medium contained 12 volume percent of a sodium tetrasulfide slution containing 34% by weight sodium tetrasulfide. The data are given in Table 7 below:

TABLE 7

| Minutes | ppm CH₃SH (outlet gas) |
|---|---|
| 0 | — |
| 25 | 5 |
| 55 | 10 |
| 85 | 15 |
| 115 | 20 |
| 145 | 30 |
| 205 | 30 |

The results from the data in Tables 6 and 7 show that, even at levels of 1000 ppm, an average of 95% of the methyl mercaptan can be removed from the gas stream if the scrubbing medium contains 6 volume percent or higher of a sodium tetrasulfide solution containing 34% by weight sodium tetrasulfide.

EXAMPLE 8

The procedure of Example 2 was followed with the exception that the gas being treated contained 100 ppm ethyl mercaptan. The data are given in Table 8 below:

TABLE 8

| Minutes | ppm C₂H₅SH (outlet gas) |
|---|---|
| 0 | — |
| 45 | 20 |
| 75 | 10 |
| 115 | 5 |
| 205 | 20 |
| 235 | 40 |
| 265 | 40 |
| 295 | 30 |
| 325 | 30 |
| 355 | 20 |

As can be seen from reviewing the data in Table 8, the aqueous scrubbing medium containing 3% by volume of the sodium tetrasulfide solution removes up to a minimum of 60% of the ethyl mercaptan originally present in the gas.

EXAMPLE 9

The procedure of Example 8 was followed with the exception that the scrubbing medium contained 12% by volume of the 34% by weight sodium tetrasulfide solution. The data are given in Table 9 below:

TABLE 9

| Minutes | ppm C₂H₅SH (outlet gas) |
|---|---|
| 0 | — |
| 45 | 40 |
| 75 | 20 |
| 115 | 20 |
| 205 | 40 |
| 235 | 60 |
| 265 | 50 |
| 295 | 40 |
| 325 | 40 |
| 385 | 40 |

The data in Table 9 show that when the scrubbing medium contains 12% by volume of the 34% by weight sodium tetrasulfide solution, a minimum of approximately 40% of the ethyl mercaptan is removed from the gas stream.

EXAMPLE 10

The procedure of Example 8 was followed with the exception that the gas being treated contained 100 parts per million of butyl mercaptan rather than 100 parts per million of ethyl mercaptan. The data are found in Table 10 below:

TABLE 10

| Minutes | ppm C₄H₉SH (outlet gas) |
|---|---|
| 0 | — |
| 45 | 10 |
| 105 | 10 |
| 165 | 20 |
| 255 | 30 |
| 315 | 20 |
| 345 | 20 |
| 405 | 20 |
| 465 | 20 |

The data in Table 10 show that a minimum of approximately 70% of the butyl mercaptan is removed using a scrubbing medium containing 3 volume percent of a sodium tetrasulfide solution containing 34% by weight sodium tetrasulfide.

EXAMPLE 11

The procedure of Example 9 was followed with the exception that the scrubbing medium contained 12% by volume of the sodium tetrasulfide (34% by weight) solution. The data are given in Table 11 below.

TABLE 11

| Minutes | ppm $C_4H_9SH$ (outlet gas) |
|---|---|
| 0 | — |
| 45 | 20 |
| 105 | 20 |
| 165 | 40 |
| 255 | 40 |
| 315 | 20 |
| 345 | 20 |
| 405 | 20 |
| 465 | 20 |

The data in Table 11 shows that a minimum of 60% of the butyl mercaptan is removed using a scrubbing medium containing the nitrite and 12 volume percent of a sodium tetrasulfide solution containing 34% by weight of sodium tetrasulfide. The data in Tables 8-11 shows that the aqueous scrubbing medium of the present invention is effective in removing ethyl and butyl mercaptans, i.e. higher mercaptans, although the removal efficiency is not as great as in the case of methyl mercaptan. This loss of efficiency in the removal of mercaptans with longer carbon chain length is believed partly due to the decreased solubility of the mercaptan in the scrubbing medium. However, the data does show conclusively that even higher mercaptans can be removed by the process and composition of the present invention.

With the addition of a water miscible solvent to increase the solubility of the higher mercaptans in the aqueous scrubbing medium, higher removal efficiencies are obtained.

As can be seen from the examples above, the process of the present invention provides an extremely effective method of removing mercaptans from gas mixtures.

The process is effective over a wide range of gas flow rates, pH values and concentrations of the active ingredients of the scrubbing medium.

The foregoing disclosure and description of the invention is illustrative and explanatory thereof, and various changes in the process and composition may be made within the scope of the appended claims without departing from the spirit of the invention.

What is claimed is:

1. A composition for removing mercaptans from a gas mixture comprising an aqueous medium containing an effective amount of an inorganic, water soluble nitrite and an effective amount of a water soluble polysulfide, said aqueous medium having an initial pH of about 10 or greater.

2. The composition of claim 1 wherein said water soluble nitrite, calculated as nitrite, is present in said aqueous medium in an amount of from about 0.1% by weight up to about saturation.

3. The composition of claim 1 wherein said water soluble nitrite is selected from the class consisting of alkaline metal nitrites, alkaline earth metal nitrites, ammonium nitrite and mixtures thereof.

4. The process of claim 3 wherein said water soluble nitrite comprises sodium nitrite.

5. The process of claim 1 wherein said polysulfide, calculated as tetrasulfide, is present in said aqueous medium in an amount of from about 0.1 to about 5% by weight of said aqueous medium.

6. The composition of claim 1 wherein said polysulfide is selected from the class consisting of alkali metal polysulfides, alkaline earth metal polysulfides and mixtures thereof.

7. The composition of claim 6 wherein said polysulfide comprises sodium tetrasulfide.

8. The composition of claim 1 wherein said aqueous medium includes a buffering agent selected from the class consisting of borates, phosphates, phthalates, bicarbonates, carbonates, ammonium chloride, and mixtures thereof.

* * * * *